US012485258B2

(12) United States Patent
Kim et al.

(10) Patent No.: US 12,485,258 B2
(45) Date of Patent: Dec. 2, 2025

(54) MICRONEEDLE ASSEMBLY

(71) Applicant: GL COMPANY Co., Ltd., Cheongju-si (KR)

(72) Inventors: Seong Ok Kim, Cheongju-si (KR); Young Sook Youn, Cheongju-si (KR); Jae Heon Kim, Cheongju-si (KR)

(73) Assignee: GL COMPANY CO., LTD., Cheongju-si (KR)

( * ) Notice: Subject to any disclaimer, the term of this patent is extended or adjusted under 35 U.S.C. 154(b) by 931 days.

(21) Appl. No.: 17/673,227

(22) Filed: Feb. 16, 2022

(65) Prior Publication Data

US 2022/0257916 A1 Aug. 18, 2022

(30) Foreign Application Priority Data

Feb. 17, 2021 (KR) ........................ 10-2021-0021095

(51) Int. Cl.
*A61M 37/00* (2006.01)

(52) U.S. Cl.
CPC . *A61M 37/0015* (2013.01); *A61M 2037/0023* (2013.01); *A61M 2037/003* (2013.01)

(58) Field of Classification Search
CPC ........ A61M 37/0015; A61M 2037/003; A61M 2037/0038; A61M 2037/0023
See application file for complete search history.

(56) References Cited

U.S. PATENT DOCUMENTS

| | | | | |
|---|---|---|---|---|
| 2005/0089554 A1* | 4/2005 | Cormier ............ | A61M 37/0015 | 424/448 |
| 2009/0030365 A1* | 1/2009 | Tokumoto ......... | A61M 37/0015 | 604/21 |
| 2013/0218084 A1* | 8/2013 | Tamaru ............ | A61M 37/0015 | 604/173 |
| 2017/0007812 A1* | 1/2017 | Onozuka ........... | A61M 37/0015 | |

FOREIGN PATENT DOCUMENTS

| | | |
|---|---|---|
| KR | 1020160150109 A | 12/2016 |
| KR | 102188397 B1 | 12/2020 |

* cited by examiner

*Primary Examiner* — Nilay J Shah
(74) *Attorney, Agent, or Firm* — Rabin & Berdo, P.C.

(57) ABSTRACT

The microneedle assembly of the present invention includes: a main body (110) opened at one side thereof and including a solution reservoir (111) formed in the opened side thereof; a dispensing unit (120) disposed at the other side of the main body (110) in such a manner as to fluidically communicate with the solution reservoir (111); a needle supports (130) positioned at a front portion of each of the dispensing units (120), and protrudingly formed at the other end of the main body (110); a microneedles (140) engaged with the front end of the needle support (130); and a first solution release flow channel (150) formed to penetrate through a portion extending outwardly from a front end of the dispensing unit (120) to the front end of the needle support (130).

2 Claims, 4 Drawing Sheets

MICRONEEDLE ASSEMBLY

CROSS-REFERENCE TO RELATED APPLICATIONS

This application claims the benefit of Korean Patent Application No. 10-2021-0021095 filed on Feb. 17, 2021 in the Korean Intellectual Property Office, which is incorporated herein by reference in its entirety.

BACKGROUND OF THE INVENTION

1. Field of the Invention

The present invention relates to a microneedle assembly which is configured to facilitate injection of a function solution such as a drug into the skin.

2. Description of Related Art

A microneedle is designed to allow a patient to give himself/herself a subcutaneous injection (i.e., self-injection), and is used to subcutaneously inject a functional solution or a drug more easily. The microneedle enables a patient to escape fear and pain of a syringe, ensures a relatively low logistics cost level, and makes it possible to accurately control the amount of a drug and deliver the drug to a certain target depth of the skin tissue between the epidermal layer and the dermal layer. For this reason, the microneedle is used in various manners.

The microneedle has slightly different application methods depending on its shapes, but as one example of these application methods, an application method shown in FIG. 1 can be used.

The application method of the microneedle as shown in FIG. 1 will be described below in more detail.

A functional solution 11 such as a drug is applied on the surface of a skin 10, and then a microneedle 12 is inserted in the skin. In this case, the microneedle 12 made of a solid body may be caused to be surface-coated with the functional solution 11 and inserted into the skin so that the drug permeates the skin.

When the microneedle 12 is inserted into the skin, a gap is formed between the microneedle 12 and the skin 10 so that the functional solution 11 permeates the gap. However, such a conventional method entails problem in that since the gap formed between the microneedle 12 and the skin 10 is narrow, making it difficult for the functional solution 11 to sufficiently permeate the skin.

In an attempt to overcome this problem, a method is also employed in which one side of a hollow microneedle is pierced into the skin and a drug is injected into the other side thereof. As an example of a method of injecting the drug into the microneedle, there has been disclosed Korean Patent No. 10-2188397 entitled "Microneedle", for which the applicant filed an application and has been granted registration, and the microneedle described in the Korean patent is shown in FIG. 2.

The microneedle 100 includes a first base 20, a second base 30 formed integrally on a top surface of the first base 20, a needle support 50 integrally formed on a top surface of the second base 30 so as to fluidically communicate with a tapered recess (H) penetrating through a bottom surface of the first base 20, and a main body 70 integrally formed at a central portion of a top surface of the needle support 50 and having a needle flow channel (h) communicating with the tapered recess.

In this case, the needle support 50 is formed in a conical shape so that it serves to press the surrounding tissue of the skin perforated by the needle main body 70 so as to help smooth perforation of the skin during a skin procedure. (19:00) (00:26)

The microneedle 100 is required to be oriented substantially perpendicular to the skin when the needle main body 70 perforates the skin. The needle main body 70 is provided in single number, and has a very small outer diameter of 40 to 300 μm. Thus, a skin procedure is required to be repeatedly performed many times in order to perform a procedure on a large area of skin, leading to an increase in the time spent in the skin procedure.

A method is also employed in which needles are arranged at uniform intervals in the form of a matrix with a plurality of rows and columns in order to reduce the number of repeated procedures.

As an example of a conventional microneedle in which a plurality of hollow microneedles are arranged in the form of an array, there has been disclosed Korean Patent Laid-Open Publication No. 10-2016-0150109 entitled "Hollow Microneedle Array".

The hollow microneedle array has an advantage in that it can reduce the time spent in a skin procedure performed on a large area of skin compared to the above-described microneedle, but still encounters a problem in that it is not provided with a needle support for pressing the surrounding tissue of the skin perforated by the needle so as to assist in smooth perforation of the skin during a skin procedure, and thus it is required that a functional solution such as a drug should be delivered to the skin tissues lying beneath the subcutaneous fat layer by perforating the subcutaneous fat using only the needle, resulting in an increase in the length of the needle.

The aforementioned conventional hollow microneedles are effective in the treatment of the skin tissues lying beneath the subcutaneous fat layer in that the functional solution such as a drug is delivered to the skin through hollow needles, but has a problem in that they have no significant effect on the subcutaneous fat.

A skin procedure may be performed in such a manner as to slightly insert the needle into the skin in order to allow the conventional hollow microneedles to have an effect on the subcutaneous fat. However, such a skin procedure involves a drawback in that it is difficult for a general user to use the skin procedure.

SUMMARY OF THE INVENTION

Accordingly, the present invention has been made to solve the aforementioned problems occurring in the prior art, and it is an object of the present invention to provide a microneedle assembly which can reduce the time spent in a skin procedure performed on a large area of skin and simultaneously can also be applied to a skin procedure performed on the subcutaneous fat.

Another object of the present invention is to provide a microneedle assembly which enables a skin procedure to be performed on the subcutaneous fat as well as the skin tissues lying beneath the subcutaneous fat.

Still another object of the present invention is to provide a microneedle assembly which enables to control the skin insertion depth of a needle depending on a user' skin conditions of a user so that a dermatologist can perform a desired skin procedure.

To achieve the above object, in one aspect, the present invention provides a microneedle assembly including: a main body opened at one side thereof, and including a solution reservoir formed in the opened side thereof to allow a functional solution to be contained therein; a dispensing unit disposed at the other side of the main body, which is a front side of the solution reservoir, in such a manner as to fluidically communicate with the solution reservoir, wherein the dispensing unit is provided in plural numbers in such a manner as to be disposed at a central portion and a peripheral portion of the main body 110 so as to be circumferentially arranged spaced apart from each other at equal radial angles so that the dispensing unit dispense the functional solution contained in the solution reservoir; a needle supports positioned at a front portion of each of the dispensing units, and protrudingly formed at the other end of the main body so that when the needle support comes into close contact with the skin, a front end thereof presses the subcutaneous fat of the skin; a microneedles engaged with the front end of the needle support so that when the microneedle comes into close contact with the skin, it is inserted into the skin; and a first solution release flow channel formed to penetrate through a portion extending outwardly from a front end of the dispensing unit to the front end of the needle support, and configured to allow the functional solution received in the dispensing unit to be delivered to the front end of the needle support therethrough so that the delivered functional solution is released to the skin tissue from the front end of the needle support therethrough via a gap formed between an outer circumference of the microneedle and the skin along the microneedle.

In the microneedle assembly of the present invention, the first solution release flow channel may be formed extending obliquely from the front end of the dispensing unit to an outer circumferential portion of the front end of the needle support.

In the microneedle assembly of the present invention, the microneedle may be formed in a conical shape and has a hollow flow channel formed therein to penetrate vertically therethrough, and the needle support may further include a second solution release flow channel formed therein so as to fluidically communicate with the hollow flow channel of the microneedle to allow the functional solution to be delivered to the skin therefrom through the hollow flow channel of the microneedle.

In addition, the main body may have any one selected from among a cylindrical shape, a quadrangular prism shape, a cylindroid shape, a rectangular prism shape, and a polygonal prism shape, and the needle support may have any one selected from between a conical shape and a polygonal pyramid shape.

Moreover, the microneedle assembly of the present invention may further include a guide engaged with the outer circumference of the main body and having a height that is lower than a front end of the microneedle and higher than a front end of the main body, the guide being configured to support the main body to ensure that the microneedle is stably inserted into the skin.

Further, the guide may enable to control the height of engagement between the guide and the main body so that the skin insertion depth of the microneedle can be controlled.

Effects of the Invention

According to the microneedle assembly of the present invention as constructed above has an advantageous effect in that since the functional solution released through the first solution release flow channel 150 is absorbed into the skin tissue via a gap formed between the microneedle 140 and the skin tissue perforated by the microneedle 140 along the microneedle 140, a cosmetic or treatment procedure can be performed on the skin tissue around the microneedle 140 as well as the time spent in a skin procedure performed on a large area of skin can be reduced.

In addition, the microneedle assembly of the present invention has an advantageous effect in that the functional solution is caused to be absorbed into the surrounding tissue of the skin perforated by the microneedle 140 through the first solution release flow channel 150, as well as the functional solution is caused to be absorbed into the surrounding tissue of the skin positioned at a front of the microneedle 140 through the microneedle 140 so that a skin procedure can be performed on the subcutaneous fat layer and the skin tissue lying beneath the subcutaneous fat layer, and a cosmetic or treatment procedure can be performed on a large area of the skin tissue perforated by the microneedle 140.

Further, the microneedle assembly of the present invention has an advantageous effect in that when the skin is perforated by the microneedles 140 during the use of the microneedle assembly and when the main body 110 comes into close contact with skin surface or the front end of the needle support 130 presses the skin surface, the main body 110 of the microneedle assembly is not stably supported by the guide 160 that is in close contact with the skin surface.

In addition, the microneedle assembly of the present invention has an advantageous effect in that since the height of engagement between the guide 160 and the main body 110 can be controlled to enable to control the depth of insertion of the microneedle 140 into the skin tissue, the depth of delivery of the functional solution to the skin tissue can be controlled depending on a user's skin conditions.

BRIEF DESCRIPTION OF THE DRAWINGS

The above and other objects, features and advantages of the present invention will be apparent from the following detailed description of the preferred embodiments of the invention when taken in conjunction with the accompanying drawings, in which.

DESCRIPTION OF REFERENCE NUMERALS

Figure 1:
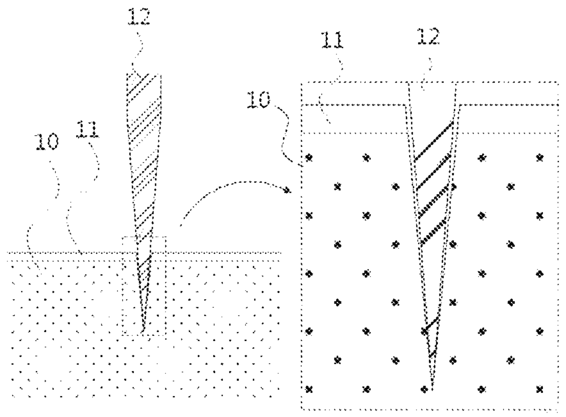
FIG. 1 RELATED ART
FIGS. 1 and 2 are cross-sectional and top perspective views showing a conventional microneedle according to the prior art.
Figure 2:
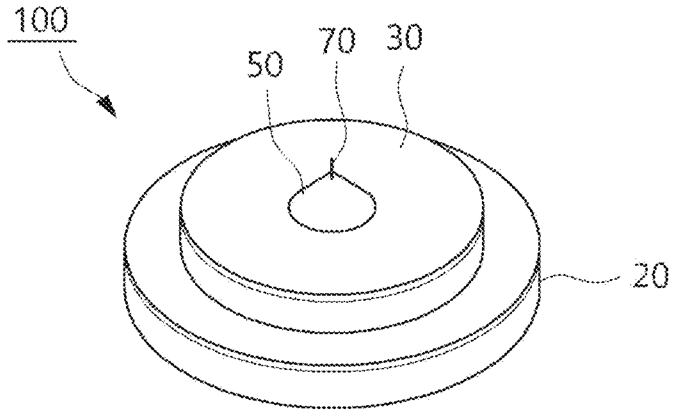
FIG. 2 RELATED ART

110: main body
111: solution reservoir
112: protrusion
120: dispensing unit
130: needle support
131: second solution release flow channel
140: microneedle
141: hollow flow channel
150: first solution release flow channel
160: guide
161: grooved recess

DETAILED DESCRIPTION OF THE PREFERRED EMBODIMENTS

Hereinafter, a monoblock brake caliper and manufacturing method thereof according to the present invention will be described in detail with reference to the accompanying drawings.

Figure 3:
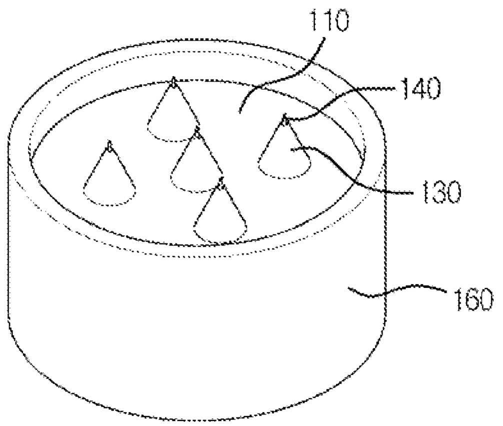
FIG. 3 is a perspective views showing a microneedle assembly according to the present invention.
Figure 4:
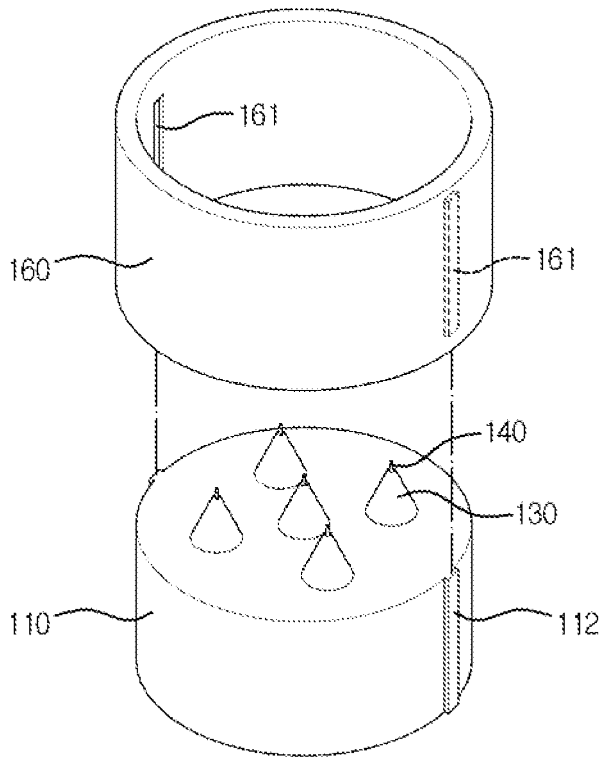
FIG. 4 is an exploded perspective view showing a microneedle assembly according to the present invention.
Figure 5:
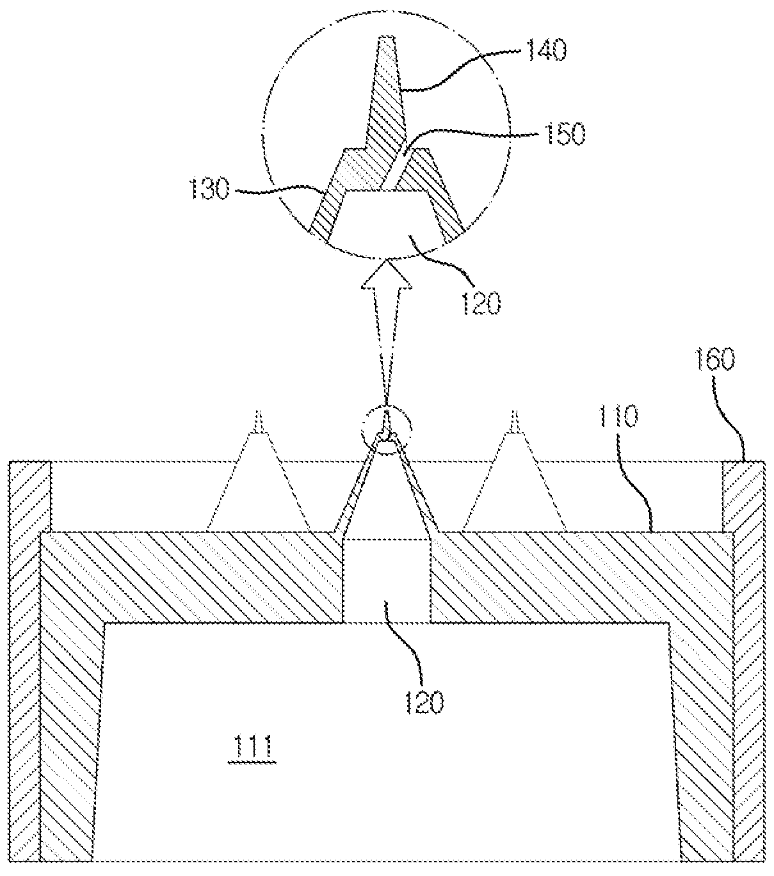
FIGS. 5 and 6 are cross-sectional views showing a microneedle assembly according to the present invention.
Figure 6:
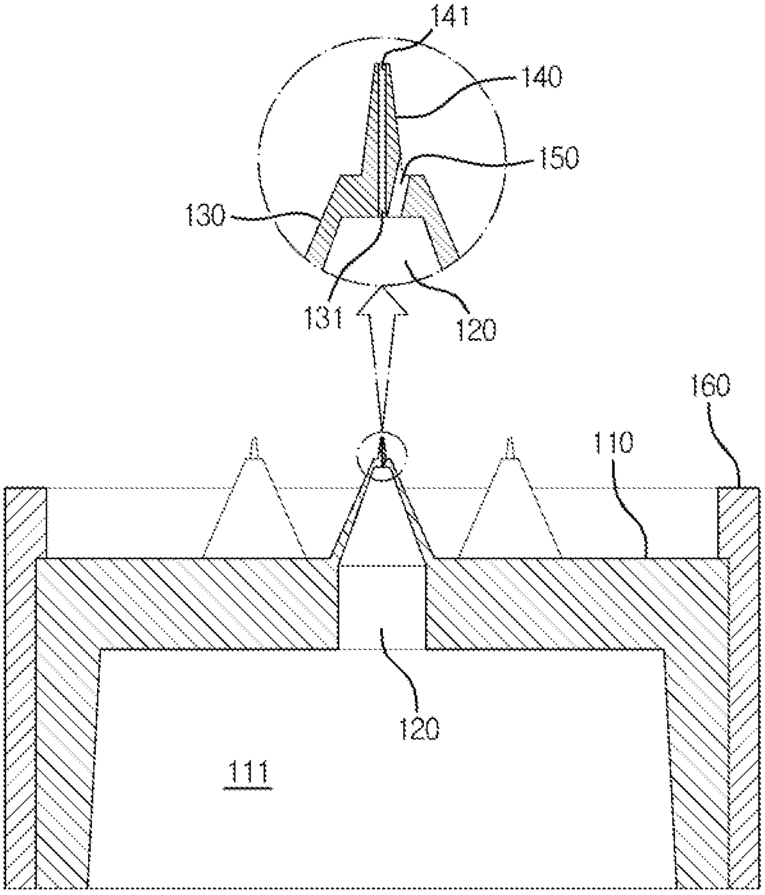

FIG. 3 is a perspective views showing a microneedle assembly according to the present invention, FIG. 4 is an exploded perspective view showing a microneedle assembly according to the present invention, and FIGS. 5 and 6 are cross-sectional views showing a microneedle assembly according to the present invention.

The microneedle assembly according to the present invention includes a main body 110; a dispensing unit 120; a needle support 130; a microneedle 140; and a first solution release flow channel 150.

The main body 110 is opened at one side thereof, and includes a solution reservoir 111 formed in the opened side thereof to allow a functional solution to be contained therein. A release means is disposed at a rear portion of the solution reservoir 111 of the main body 110 so as to allow the functional solution contained in the solution reservoir 111 to be released thereby to the dispensing unit 120 and the first solution release flow channel 150, which will be described later. As the release means, a cylinder and a piston rod described in Korean Patent Laid-Open Publication No. 10-2019-0111682 entitled "Hollow Microneedle Array for Injector, Injector Including the Same, and Manufacture Method of Microneedle Array for Injector" may be used, and any other release means known in the art may be used to release the solution.

The solution reservoir 111 fluidically communicates with a plurality of dispensing units 120 which will be described later. The solution reservoir is provided in single number and fluidically communicates, at a front end thereof, with the plurality of dispensing units 120 (see FIGS. 5 and 6).

An inner circumferential surface of the solution reservoir 111 is preferably formed in a tapered shape which is gradually reduced in diameter as it goes in a direction where the solution is released (see FIGS. 5 and 6).

The dispensing unit 120 is disposed at the other side of the main body 110, which is a front side of the solution reservoir 111, in such a manner as to fluidically communicate with the solution reservoir 111. The dispensing unit 120 is provided in plural numbers in such a manner that two or fifteen dispensing units are disposed at a central portion and a peripheral portion of the main body 110 so as to be circumferentially arranged spaced apart from each other at equal radial angles so that the dispensing unit 120 can serve to dispense the functional solution contained in the solution reservoir 111. The dispensing unit 120 is formed in a cylindrical shape so as to fluidically communicate with the solution reservoir 111, and a front end of a portion of the dispensing unit 120 fluidically communicating with the solution reservoir 111 is formed in a sharp conical shape like the needle support 130 which will be described as shown in FIGS. 5 and 6 so that the functional solution delivered thereto from the solution reservoir 111 is received in the dispensing unit 120 so as to be dispensed in a direction in which the needle support 130 is positioned The needle support 130 is positioned at a front portion of each of the dispensing unit 120 in such a manner as to be protrudingly formed at the other end of the main body 110 so that when the needle support 130 comes into close contact with the skin, a front end thereof presses the subcutaneous fat of the skin. The microneedle 140 is engaged with a front end of the needle support 130. When the needle support 130 is caused to press the skin, the skin insertion depth of the microneedle 140 can be increased.

The microneedle 140 is engaged with the front end of the needle support 130 so that when the microneedle 140 comes into close contact with the skin, it is inserted into the skin. The needle support 130 is preferably made of a synthetic resin material, and the microneedle 140 is preferably formed integrally with the needle support 130.

The first solution release flow channel 150 is formed to penetrate through a portion extending outwardly from a front end of the dispensing unit 120 to the front end of the needle support 130, and allows the functional solution received in the dispensing unit 120 to be delivered to the front end of the needle support 130 therethrough so that the delivered functional solution is released to the skin tissue from the front end of the needle support 130 therethrough via a gap formed between an outer circumference of the microneedle 140 and the skin along the microneedle 140.

The functional solution released to the skin tissue through the first solution release flow channel 150 is absorbed into the skin tissue via a gap formed between the microneedle 140 and the skin tissue perforated by the microneedle 140 along the microneedle 140.

As such, the functional solution released through the first solution release flow channel 150 is absorbed into the skin tissue via the gap formed between the microneedle 140 and the skin tissue perforated by the microneedle 140 along the microneedle 140, the cosmetic or medical treatment effect on the skin tissue around the microneedle 140 occur.

In this case, in order to facilitate the release of the functional solution through the first solution release flow channel 150, the first solution release flow channel 150 is preferably formed extending obliquely from the front end of the dispensing unit 120 to an outer circumferential portion of the front end of the needle support 130 as shown in FIGS. 5 and 6.

The first solution release flow channel 150 may be provided in single number. In order for the functional solution to be uniformly absorbed into the skin tissue around the microneedle 140 upon the release of the functional solution through the first solution release flow channel 150, the first solution release flow channel 150 may be provided in plural numbers (two or four) to extend radially at equal angles from the front end of the dispensing unit 120 to the outer circumferential portion of the front end of the needle support 130.

In this case where the number of the first solution release flow channels 150 provided is 1, the functional solution may be delivered to the microneedle 140 positioned at an opposite side to the release direction of the functional solution in a less amount compared to the case where the first solution release flow channel 150 is provided in plural numbers.

If the number of the first solution release flow channels 150 extending radially at equal angles from the front end of the dispensing unit 120 to the outer circumferential portion of the front end of the needle support 130 exceeds four, the strength of the needle support 130 that supports the microneedle 140 becomes relatively low due to a very great increase in the number of the first solution release flow channels 150, and thus there is a high risk that the needle support 130 will be collapsed. Therefore, it is desirable to limit the number of the first solution release flow channels 150.

The present invention enables the functional solution to be absorbed into the surrounding tissue of the skin perforated by the microneedle 140 through the first solution release flow channel 150, as well as enables the functional solution to be absorbed into the surrounding tissue of the skin positioned at a front of the microneedle 140 through the microneedle 140.

To this end, as shown in FIG. 6, the microneedle 140 is formed in a conical shape and has a hollow flow channel 141 formed therein to penetrate vertically therethrough, and the needle support 130 further include a second solution release flow channel 131 formed therein so as to fluidically communicate with the hollow flow channel 141 of the microneedle 140 to allow the functional solution to be delivered to the skin therefrom through the hollow flow channel 141 of the microneedle 140.

The main body 110 may be formed in various shapes, preferably may have any one selected from among a cylindrical shape, a quadrangular prism shape, a cylindroid shape, a rectangular prism shape, and a polygonal prism shape. Among them, in the case where the main body 110 has the cylindroid shape or the rectangular prism shape, the microneedles 140 are also arranged in a row according to the arrangement of the needle supports 130 in a row so that the microneedles 140 can be applied to the skin care or treatment of a skin site with a narrow width.

Preferably, the needle support 130 has any one selected from between a conical shape and a polygonal pyramid shape. The reason why the needle support 130 is formed in the conical shape is that the needle support 130 easily presses the subcutaneous fat.

When the skin is perforated by the microneedle 140 of the microneedle assembly to deliver the functional solution to the skin tissue, the microneedle 140 is preferably oriented perpendicular to the skin surface. In addition, when the skin is perforated by the microneedle 140 of the microneedle assembly, the main body 110 is caused to come into close contact with the skin surface or the front end of the needle support 130 is caused to press the skin surface so that the functional solution can be delivered into the skin tissue.

In this case, in the case where the skin surface is flat, there is caused no problem, but in most case, the skin surface is not in a flat state. When the skin is perforated by the microneedles 140 during the use of the microneedle assembly and when the main body 110 comes into close contact with skin surface or the front end of the needle support 130 presses the skin surface, there occurs a problem in that the main body 110 of the microneedle assembly is not stably supported. In addition, when the functional solution is delivered to the skin after the perforation of the skin by the microneedle 140, there also occurs a problem in that the main body 110 of the microneedle assembly may shake.

In order to solve such problems, the microneedle assembly of the present invention adopts a guide 160 engaged with the main body 110 to support the main body 110 (see FIGS. 3 and 4).

The guide 160 is engaged with the outer circumference of the main body, has a height that is lower than a front end of the microneedle 140 and higher than a front end of the main body 110, and support the main body 110 while coming into close contact with the skin to ensure that the microneedle 140 is stably inserted into the skin.

In this case, preferably, the guide 160 enables to control the height of engagement between the guide 160 and the main body 110 so that the skin insertion depth of the microneedle 140 can be controlled.

The guide 160 and the main body 110 may be engaged with each other, for example, in a screw-engagement manner.

Alternatively, the engagement between the guide 160 and the main body 110 may be achieved, for example, by the cooperative operation between a protrusion 112 formed longitudinally on the outer circumferential surface of the main body 110 and a grooved recess 161 formed longitudinally on the inner circumferential surface of the guide 160 so as to be engaged with the protrusion 112 (see FIG. 4).

The guide 160 may be made of an elastic material so as to cause less skin irritation upon contact between the guide 160 and the skin.

The technical spirit of the present invention should not be construed by limiting the present invention to the above-mentioned embodiments. The application range thereof is of course varied, and various modifications thereof may be made by those skilled in the art without departing from the gist of the present invention. Therefore, as long as these modifications and changes are apparent to those skilled in the art, they fall within the protection scope of the present invention.

What is claimed is:

1. A microneedle assembly comprising:

a main body (110) opened at one side thereof, and including a solution reservoir (111) formed in the opened side thereof to allow a functional solution to be contained therein;

a dispensing unit (120) disposed at another side of the main body (110), which is a front side of the solution reservoir (111), in such a manner as to fluidically communicate with the solution reservoir (111), wherein the dispensing unit (120) is provided in plural numbers in such a manner that the plural numbers are disposed at a central portion and a peripheral portion of the main body 110 so as to be circumferentially arranged spaced apart from each other at equal radial angles so that the dispensing unit (120) dispenses the functional solution contained in the solution reservoir (111);

a needle support (130) positioned at a front portion of each of the plural number of the dispensing unit (120), and protrudingly formed at another end of the main body (110) so that when the needle support (130) comes into close contact with skin, a front end of the needle support (130) presses subcutaneous fat of the skin;

a microneedle (140) engaged with the front end of the needle support (130) so that when the microneedle (140) comes into close contact with the skin, the microneedle (140) is inserted into the skin; and a first solution release flow channel (150) formed to penetrate through a portion extending outwardly from a front end of the dispensing unit (120) to the front end of the needle support (130), and configured to allow the functional solution received in the dispensing unit (120) to be delivered to the front end of the needle support (130) through the first solution release flow channel (150) so that the delivered functional solution is released to skin tissue from the front end of the needle support (130) through the first solution release flow channel (150) via a gap formed between an outer circumference of the microneedle 140 and the skin along the microneedle (140);

wherein the first solution release flow channel (150) is formed extending obliquely from the front end of the dispensing unit (120) to an outer circumferential portion of the front end of the needle support (130);

wherein the microneedle (140) is formed in a conical shape and has a hollow flow channel (141) formed therein to penetrate vertically therethrough, and the needle support (130) further comprises a second solution release flow channel (131) formed therein so as to fluidically communicate with the hollow flow channel (141) of the microneedle (140) to allow the functional solution to be delivered to the skin therefrom through the hollow flow channel (141) of the microneedle (140); and wherein the first solution release flow channel (150) and a combined channel formed by the second solution release flow channel (131) and the hollow flow channel (141) extend from a same upper inner surface of the needle support 130, the combined channel is perpendicular to the upper inner surface of the needle support 130 and the obliquely extending first solution release flow channel (150) extends away from combined channel at an angle with respect to the upper inner surface of the needle support (130).

2. The microneedle assembly according to claim 1, further comprising a guide (160) engaged with an outer circumference of the main body and having a height that is lower than a front end of the microneedle (140) and higher than a front end of the main body (110), the guide being configured to support the main body 110 to ensure that the microneedle 140 is stably inserted into the skin.

* * * * *